United States Patent [19]

Ehrenfeld

[11] Patent Number: 5,021,234
[45] Date of Patent: Jun. 4, 1991

[54] AGENT AND PRODUCT FOR THE DIAGNOSIS AND TREATMENT OF TUMORS AND FOR THE TREATMENT OF WEAKNESSES OF THE CELLULAR AND HUMORAL IMMUNE DEFENSE

[76] Inventor: Udo Ehrenfeld, Furtmayrstr. 20, 8400 Regensburg, Fed. Rep. of Germany

[21] Appl. No.: 485,757

[22] Filed: Feb. 26, 1990

Related U.S. Application Data

[63] Continuation of Ser. No. 689,728, Jan. 8, 1985, abandoned, which is a continuation-in-part of Ser. No. 557,738, Dec. 2, 1983, abandoned.

[30] Foreign Application Priority Data

Sep. 26, 1983 [DE]  Fed. Rep. of Germany ....... 3334751
Oct. 7, 1983 [DE]   Fed. Rep. of Germany ....... 3336583
Jan. 24, 1984 [DE]  Fed. Rep. of Germany ....... 3402312

[51] Int. Cl.$^5$ ................... A61K 49/02; A61K 37/22; C12N 1/00; C12N 1/20
[52] U.S. Cl. ........................................ 424/1.1; 424/9; 424/450; 435/832; 435/872; 435/879
[58] Field of Search ........................ 424/1.1, 450, 9; 435/832, 873, 879; 436/829; 514/885

[56] References Cited

U.S. PATENT DOCUMENTS 4,029,762  6/1977  Galanos et al. ..................... 530/387

FOREIGN PATENT DOCUMENTS

83/03383  10/1983  World Int. Prop. O. .

OTHER PUBLICATIONS

Osborn et al., "Incorporation of Lipid Vesicles by Salmonella", Ann., N.Y.; Acad. Sci., 308, pp. 215–225, 1978.
Chemical Abstracts, Band 98, Nr. 25, 20, Jun. 1983; p. 425, "The activation of tumoricidal properties in macrophages of endotoxin responder etc." & J. Reticuloendothel. Soc. 1983; 33(3), 165–174.
The Journal of Immunology, Band 130, Nr. 4, Apr. 1983; pp. 1500–1502, "The activation of human monocytes by liposome-encapsulated muramyl etc.".
Biological Abstracts, Band 6; Nr. 7; 1983, "In vitro effects of lipopolysaccharides and mycobacterial etc." & Res. Vet. Sci. 34(2); pp. 212–217, 1983.
Biological Abstracts, Band 62, Nr. 6; 1975; "Cell walls of mycrobacteria and related organisms: Chemistry and etc." & Mol Cell. Biochem. 7(2), pp. 87–104, 1975.
Chemical Abstracts, Band 91, Nr. 23, Dec. 3, 1979; p. 57, "Evaluation of the immunomodulator administration etc." & Gan To Kagaku Ryoho 1979; 6(Rinji Zokan 2), 219–230.
Inspection and Immunity, Feb. 1975; pp. 257–264, "Isolation of Mitogenic and Adjuvant Active Fractions etc." by Rita Ciorbaru et al.

Primary Examiner—John S. Maples
Attorney, Agent, or Firm—Ostrolenk, Faber, Gerb & Soffen

[57] ABSTRACT

An agent for the diagnosis and treatment of malignant tumors and for the treatment of lowered cellular and humoral immune defense is described which contains an immune modulator, a lipopolysaccharide or an immune modulator tagged with a radioactive tracer, a dyestuff or a cytostatic, or a similar polysaccharide, possibly in and/or on liposomes or lipidized. There is also described a product which contains the agent together with an adjuvant consisting of an aldehyde and an alcohol. There is also described a method for the diagnosis of malignant tumors comprising the step of administering to a mammal a diagnostic effective amount of the agent, optionally together with an adjuvant consisting of an aldehyde and an alcohol.

14 Claims, No Drawings

AGENT AND PRODUCT FOR THE DIAGNOSIS AND TREATMENT OF TUMORS AND FOR THE TREATMENT OF WEAKNESSES OF THE CELLULAR AND HUMORAL IMMUNE DEFENSE

This is a continuation of Ser. No. 06/689,728 filed on Jan. 8, 1985, now abandoned. which is a continuation-in-part of application Ser. No. 557,738, filed Dec. 2, 1983, now U.S. Pat. No. 4,590,060.

The invention relates to an agent and a product containing the agent for the diagnosis and treatment of malignant tumors as well as for the treatment of weaknesses in the cellular and humoral immune defense.

The diagnosis and treatment of malignant tumors is still difficult today despite intensive research. It is practically impossible to recognize malignant tumors at an early stage and up to now there has been no method available by which an early diagnosis can be effected. The treatment of malignant tumors is—as is universally known—not satisfactory.

U. Ehrenfeld reports (Krebsgeschehen 5, 132 et seq. (1979)) on the cancerotoxic effect of a mixture of acetaldehyde and ethanol. The mixture contains 3 to 10 g of acetaldehyde per 1000 g of ethanol. It has been found, however, that the action of this mixture is not sufficient for the treatment of solid malignant tumors or of metastases.

It is known to use liposomes as carriers of medication and markers and to concentrate them in certain organs. It has beer found that intravenously employed liposomes as carriers of medication are not able to pass continuously through capillary walls and are taken up rapidly by phagocyting cells (G. Poste, Biol. of the Cell 47, 19 (1983)).

Such liposomes can also not leave the circulation and are therefore not suitable to serve as direct carriers or markers or medications for tumors. A simple administration of liposomes by inhalation has failed in the past as a result of the fact that the alveola wall of the lung could not be penetrated by the liposomes within the time available.

Attempts have also been made to intravenously inject liposomes which contain immune modulators. This method seemed successful in animals. Since the liposomes, as mentioned above, cannot leave the circulation without the help of the cells, this method, however, has not been suitable up to now for diagnosis and therapy in humans.

There is a great need for an agent which is able to pass through cell walls, such as, for instance, the cell walls of the lung, of the blood vessels, of the lymph vessels, etc. so that it is possible for it, alone or possibly bearing a drug, to act directly on malignant tumors or eliminate weaknesses in cell defense.

The diagnosis of malignant tumors is frequently extremely difficult. Malignant tumors can only be detected by x-ray after they have reached a given size. The formation of small tumors and metastases can frequently not be detected, with the result that an early recognition of tumors is not possible and that malignant tumors frequently can be only incompletely removed upon surgery. Therefore, there is a need for a method of diagnosis by which even small tumors can be detected and recognized in a simple and easy manner.

During the last few years increased attention has been paid to lowered immune defense which occurs for various reasons. The lowering of the defense against infectious diseases is caused, in part, by environmental poisons such as lead, sulfur oxides, nitrogen oxides, cadmium and an impoverishment of copper in the diet.

For the treatment of humoral lowered immune defenses, immune globulin concentrates are used. For the treatment of cellular lowered immune defenses, HLA-like cell concentrates are used. However, they are available only to an extremely slight extent and have an extremely short life so that this last-mentioned therapy necessarily remains generally unsuccessful.

The purpose of the present invention is to provide an agent and a product for the diagnosis and treatment of malignant tumors. The agent should be highly effective so that it can therefore be administered in lower concentrations than the known agents. The agent of the invention is to result in less severe stress on the patient's organism and furthermore its administration in simple fashion is to be possible.

In accordance with the invention, an agent is to be made available by which lowered immune defenses in man and animal can be successfully treated. The agent is to be of unlimited availability and simple to use. It is to be easily dosed. Non-toxic antidotes for the agent are available on the market; cortisol and agents which result in the production of cortisol counteract it. Surprisingly, it has now been found that immune modulators and lipopolysaccharides are able, particularly when used orally, and especially when administered by inhalation, to pass through cell walls. In this way a new method of recognizing malignant tumors and a new method of treating them is possible.

The object of the present invention is an agent for the diagnosis and treatment of malignant tumors and for the treatment of weaknesses of the cellular and humoral immune defenses, the agent being characterized by the fact that, in addition to ordinary excipients and/or diluents, it contains (1) an immune modulator
  (a) in and/or on liposomes or
  (b) lipidized, or
(2) a lipopolysaccharide
  (a) in and/or on liposomes or
  (b) lipidized, or
(3) an immune modulator tagged with a radioactive tracer, a dyestuff or a cytostatic, or a mixture of such tagged immune modulators, or
(4) an immune modulator tagged with a radioactive tracer, a dyestuff or a cytostatic, or a mixture of such tagged immune modulators
  (a) in and/or on liposomes or
  (b) lipidized, or
(5) a lipopolysaccharide tagged with a radioactive tracer, a dyestuff or a cytostatic, or a mixture of such tagged lipopolysaccharides, or
(6) a lipopolysaccharide tagged with a radioactive tracer, a dyestuff or a cytostatic or a mixture of lipopolysaccharides tagged in this manner,
  (a) in and/or on liposomes, or
  (b) lipidized, or
(7) a mixture of two or more of the following compounds:
  an immune modulator,
  a lipopolysaccharide,
  an immune modulator tagged with a radioactive tracer, a dyestuff or a cytostatic, or
  a lipopolysaccharide tagged with a radioactive tracer, a dyestuff or a cytostatic, (8) a mixture of two or more of the following compounds:
an immune modulator,
a lipopolysaccharide,
an immune modulator tagged with a radioactive tracer, a dyestuff or a cytostatic, or
a lipopolysaccharide tagged with a radioactive tracer, a dyestuff or a cytostatic
(a) in and/or on liposomes, or
(b) lipidized.

The object of the invention is furthermore a product containing
(a) an adjuvant which, in addition to ordinary pharmaceutically acceptable excipients and/or diluents, contains an aldehyde of formula I

RCHO        (I)

in which R is a hydrogen atom or a straight-chain or branched hydrocarbon group having 1 to 4 carbon atoms, in which connection the free aldehyde may also be metabolically liberated directly or indirectly by substances, and
(b) an agent such as mentioned above, for the simultaneous, separate or stepwise application in time upon the diagnosis and treatment of malignant tumors and for the treatment of lowered immune defenses.

The agent, surprisingly, easily passes through the cell walls, and particularly through the walls of lung alveoli, and lymph and blood capillaries. In this way a new diagnosis and a novel method of treating malignant tumors is made possible since the immune modulators and/or lipopolysaccharides charged with a radioactive tracer pass directly to the malignant tumor and produce there the highest possible effect for the recognition and treatment of the tumor.

The agent of the invention can be used for the diagnosis of malignant tumors in vivo and in vitro. The malignant tumors can be diagnosed outside the body. For instance, the surgeon can remove malignant tissue in an operation and then incubate the living tissue outside the body so that in the flat, cut section of the tissue, e.g. upon color marking with fluorescein isothiocyanate, malignant tissue lights up in UV light and can be immediately distinguished from the dark, healthy tissue.

With the agent in accordance with the invention it is possible to accurately characterize tumor sizes on the order of 100 to 10,000 cells; with additional administration of oxygen the agent is capable, on basis of the minimal radioactive radiation introduced for the diagnosis, to produce an active inflammation as a result of radiation destruction of tumor tissue.

As immune modulators and lipopolysaccharides there can be used in the present invention all compounds which are available on the market and are described in the literature.

By "immune modu-lators" also known as "immune stimulants," there are understood compounds or mixtures which stimulate the immune system in any way.

The immune modulators are not clearly defined in the literature. Certain lipopolysaccharides may also fall under the concept of immune modulators. In the present application, however, the lipopolysaccharides are treated as a separate class of compounds since the definitions of immune modulators and lipopolysaccharides have not yet been clearly established in the literature.

In accordance with the invention those compounds which are already used in treatment or diagnosis in humans are preferably used as immune modulators.

There are particularly preferred in accordance with the invention muramylic acid dipeptide derivatives (MDP) or peptidoglycans or peptidoglycan-free extracts, for instance of a polysaccharide structure, such as extracts from Nocardia rubra or Nocardia opaca or from other bacteria, and preferably from Calmette Guerin bacillus (BCG), as well as detoxified preparations from salmonella as well as lipidized polysaccharides, preferably lipidized, those from salmonella preparations which are detoxified by removal of appended groups and are thus available suitable for use on humans for the said effects, and their derivatives.

The immune modulators may be of natural origin, i.e. left in natural state, or be semisynthesized or synthesized substances.

The peptidoglycans designated as immune modulators consist of a polysaccharide skeleton which is built up of disaccharide blocks of N-acetylglucosaminyl-N-acylmuramyl in which the acyl group is formed by an acetyl or glycolyl group. These units would have to be present in sufficient number for the desired effect. In addition to these units, there may also be present 0 to 10% neutral sugar. These peptidoglycans contain peptide substituents which have lost their interpeptide bonds to such an extent that they have become water-soluble and are still only slightly soluble in fat.

No peptide substituents should be present any longer at the end of the glycan chains. The peptidoglycans should be entirely free of natural lipids, together with which they are present in the bacterial walls. These lipids could, however, in one preferred embodiment of the agent of the invention, be replaced by other lipids, for instance phosphatidyl choline alone or together with phosphatidyl serine and cholesterol in a molar ratio of 8:2:10, in which connection the water solubility of the peptidoglycan is to be retained.

These last-mentioned lipids can be present as solvents or bound to peptidoglycans. The N-acetylglucosamine groups of the peptidoglycans may be partially desacetylated. The entire molecule can, however, also be reacted, in addition, with aldehydes of formula I

RCHO        (I)

in which R is a hydrogen atom or a straight-chain or branched hydrocarbon group having 1 to 4 carbon atoms. They are preferably reacted with acetaldehyde.

The peptide units of the peptidoglycans which are bonded by L-alanin contain sequences of L-alanin→D-isoglutamine→meso-$\alpha$-$\epsilon$-diamino-pimelic acid (DAP), the DAP being possibly amidized. In their place, uridine diphosphate may also be present or, as existing in the nature, another amino acid such as, for instance, lysine, which in its turn may be substituted.

The above-mentioned change in the peptidoglycans, such as a lipidization and introduction of other peptide substituents, such as, for instance, UDP and others, as well as the use of other polysaccharide chains with the same effect and similar introduction of substituents, leads to lipopolysaccharides which can also be used in accordance with the invention.

The immune modulators and lipopolysaccharides may also be treated with human albumin and/or immune globulin and in this way be administered intravenously or intralymphatically. Administration in liposomes is preferred here.

According to the invention, the immune modulators and lipopolysaccharides may be tagged with a radioactive tracer. Tagging with a radioactive tracer is described in the literature (M.P. Osborne, V.J. Richardson, K. Jeyasingh and B.E. Ryman, Int. J. Nucl. Med. Biol. 6, 75 (1979)).

Examples of radioactive tracers are the tracers which are customarily used in the field of treatment and diagnosis such as, for instance, 99 m Tc, 25 to 200 mCi, since, upon the closed inhalation system which is required by the manner of use, more than 50% of the radioactivity remains in this system and high lung loads are unnecessary.

The immune modulators and lipopolysaccharides may furthermore bear a cytostatic. Examples of cytostatics and metastasis inhibitors which can be used according to the invention are all compounds at present known as cytostatics and metastasis inhibitors. Examples thereof are melphalan, carmustin, lomustin, cyclophosphamide, estramustine phosphate, ifosfamide, chlorambucil, methrotrexate, pegafur, flourouracil as well as antibiotics which are used for this purpose.

The immune modulators and lipopolysaccharides may furthermore be tagged with a dyestuff. As dyestuffs there are suitable, for instance, ordinary commercial amino group tagging dyestuffs which are non-toxic to humans such as, inter alia, fluorescein isothiocyanate. From the corresponding dyestuff, for instance fluorescein isothiocyanate, a number of molecules are mixed with the preparation of the immune modulator indicated for the treatment which is clearly below the number of amino groups present therein. The mixture is then set aside for 45 minutes at 37° C.

According to the invention, it is also possible to use mixtures of one or more immune modulators, those which are tagged with a radioactive tracer, a dyestuff or a cytostatic, as well as mixtures of lipopolysaccharide and, as mentioned above, tagged lipopolysaccharide. One can also use mixtures of immune modulators, possibly tagged immune modulators and lipopolysaccharides, possibly tagged lipopolysaccharides.

According to the present invention it is preferred that the immune modulators and/or lipopolysaccharides, or the tagged immune modulators and/or lipopolysaccharides, resp., not be used alone but, rather, together with liposomes or in lipidized form.

Liposomes are spherical structures of one or more lipid double layers with an inner space. Such vesicles can be produced by extremely fine mechanical division of phospholipids, such as lecithin, in aqueous media.

According to the invention, liposomes are used which are single, unilamellar vesicles (SUV) and consist preferably of phosphatidyl choline: phosphatidyl serine: cholesterol in a molar ratio of 8:2:10 and are prepared by sonication. The lipids from which they are prepared are available on the market, for instance from Sigma Products. They are purified by column chromatography, dissolved in ether, evaporated under $N_2$, mixed with the immune modulator or the charged immune modulator, suspended again in phosphate-buffered saline solution (PBS), for instance at a pH of 7.4, and then sonicated for instance for 25 minutes at +2° C. with a pulsated Branson 15 sonicator. The sonication is carried out under $N_2$.

After the sonication, the liposomes are chromatographed on a Sepharose 4 B column and the fraction of the population with radii less than 300Å are preferably used (C. Huang, Biochemistry 15, 2362 (1969)). These liposomes are then tagged for diagnosis in known manner with preferably 99 m Tc on the immune modulator in accordance with Osborne et al. (M.P. Osborne, V.J. Richardson, K. Jeyasingh and B.E. Ryman, Int. J. Nucl. Med. Biol. 6, 75 (1979)).

In order to check the radioactive labelling, an aliquot portion of the liposomes is introduced into a Sepharose-4-B column and chromatographed. It is found that the preparation has a specific activity of 99.2% of radioactivity bound to immune modulator and 0.8% free pertechnetate.

The liposomes can be charged with immune modulators which are charged with a radioactive tracer, with a dyestuff, a cytostatic or mixtures of these compounds. Such liposomes are particularly suited for diagnosis.

The preparation of lipopolysaccharides in or on liposomes is effected in a manner similar to the preparation of liposomes charged with the immune modulators.

According to another preferred embodiment of the invention, the immune modulator or the lipopolysaccharides are possibly, as explained above, charged dispersed in a lipid. The dispersing takes place by bringing the substances together and subjecting them also to sonication.

Differing from the above-indicated preparation of the liposomes, for example:

(1) the evaporation of the lipids dissolved in this connection in ethanol and in ether under $N_2$ is dispensed with;

(2) after the sonication, the chromatographing and the separation of the fractions with radii of more than 300Å is dispensed with and this product is used only for inhalation.

As lipids one can use phosphatidyl choline alone or together with phosphatidyl serine and cholesterol, for instance in a molar ratio of 8:2:10.

As mentioned above, it is known that a mixture of acetaldehyde and ethanol has a cancerotoxic effect. Surprisingly, it has now been found that the agent of the invention develops a particularly good action when it is administered together with an adjuvant. The adjuvant contains, in addition to ordinary excipients and/or diluents, an aldehyde of formula I

RCHO  (I)

in which R is a hydrogen atom or a straight-chain or branched hydrocarbon group having 1 to 4 carbon atoms. It is particularly preferred if the adjuvant contains, in addition to the aldehyde of formula I, an alcohol of formula II $R^1CH_2OH$  (II)

in which $R^1$ has the meaning indicated above for R.

The invention thus also relates to a product which contains the above-mentioned agent and the adjuvant described above. Surprisingly, it has been found that upon the simultaneous and time-staggered use of the adjuvant together with the agent of the invention the effectiveness of the agent of the invention is even substantially improved.

The adjuvant in the product of the invention may contain the aldehyde as such in ordinary pharmacologically compatible excipients and/or diluents. It is particularly preferred to use the aldehyde in aqueous and/or alcoholic solution. According to the invention, it is particularly preferred in this connection to use the aldehyde in question together with its corresponding alcohol.

Preferred adjuvants liberate, indirectly or directly, and/or contain formaldehyde/methanol, acetaldehyde/ethanol, n-propionaldehyde/n-propanol, isopropionaldehyde/isopropanol, n-butyraldehyde/n-butanol, isobutyraldehyde/isobutanol, tert-butyraldehyde/tert-butanol, n-valeraldehyde/n-pentanol or mixtures of these compounds.

An optimum effect of the new pharmaceutical preparation, inter alia, an improvement in the permeability for charges of lipoles, is obviously obtained when the concentration of the aldehyde in the body can be maintained high for long periods of time, and preferably uniformly high. It is known that ethanol is degraded to acetaldehyde in the human body, the rate of degradation of the ethanol above a certain concentration, in the same way as that of the acetaldehyde, being practically independent of the concentration and the rate of degradation of the acetaldehyde being evidently of the same magnitude or somewhat less than that of the ethanol. This concentration of acetaldehyde which occurs upon the natural degradation of alcohol is, however, clearly not high enough.

With the adjuvant it is possible, on the one hand, to develop within the body of a patient suffering from tumors and/or metastases a sufficiently high concentration of, for instance, acetaldehyde, in which connection, by means of the preferred embodiment of the invention by the simultaneous administration of a substance which is as non-injurious as possible—particularly corresponding alcohols—by the degradation of which the corresponding aldehyde is continuously reformed, which favors the improvement in the passage through cells and tissues as well as the direction of action of the lipidized immune modulator for the cell immune defense.

The acetaldehyde/ethanol pair is practically non-toxic; it can be administered in suitably high doses. From this there results the possibility of long-term treatment, even in combination with radiation treatment. The immunobiological system is influenced positively and a combination with other medicaments as well as with surgical and radiological measures is possible.

In addition to this ethanol/acetaldehyde mixture, other analogous mixtures of the above-mentioned type are also fundamentally possible, such as methanol/formaldehyde, propanol/propanal, butanol/butanal, etc. Methanol is degraded substantially more slowly in the human body than ethanol, and propanol is degraded two times faster than ethanol. The agent may in each case contain only one specific selected aldehyde, as well as mixtures of aldehydes. The use of aldehydes is not necessarily coupled with the presence of the corresponding alcohols. Aqueous solutions of the aldehydes can also be used. Instead of the free aldehydes there may also be used in the invention those aldehyde derivatives which form the free aldehyde in the metabolism of the patient treated with the pharmaceutical agent of the invention. Suitable aldehyde derivatives are, for instance, the acetals or semiacetals or condensation products, which may also be used as is or in dissolved form (water or alcohols) as well as in mixtures with the aldehydes and/or alcohols.

In another preferred embodiment of the invention, the adjuvant contains small amounts (less than 0.05 wt%) of peroxides, there entering into consideration, in particular, peroxides of related composition, especially $H_2O_2$ and/or aldehyde peroxide or hydroxy hydroperoxide, resp., as well as the peroxide of the corresponding carboxylic acid. The anti-tumor action is still further improved by the content of peroxides.

The concentration of aldehyde in the preparation of the invention is determined, on the one hand, by its compatibility and, on the other hand, by the dose to be administered. For the pair ethanol/acetaldehyde, an acetaldehyde concentration in the alcohol of less than $2 \times 10^{-4}$ mole/liter is frequently unsatisfactorily slow in its action. The action increases with an increase in the concentration of aldehyde and its upper limit is formed in the individual case, as a rule, by incompatibility of the acetaldehyde which may possibly occur. In practice, for instance, ethanol/acetaldehyde solutions with $5 \times 10^{-2}$ mole to 1 mole acetaldehyde per liter of ethanol have proven satisfactory, it being possible to use these mixtures in a dose of, for instance, 10 to 150 cc per day.

It is preferred that the adjuvant contain 10 to 40 g of aldehyde per 1000 g of alcohol, while 15 to 30 g of aldehyde per 1000 g of alcohol is particularly preferred. In general, the adjuvant is diluted with water for administration. The alcoholic solution may be diluted with any amount of water as desired. For example, one volume of the alcoholic solution can be diluted with 1 to 10 volumes, and preferably 2 to 5 volumes, of water.

The adjuvant is preferably administered orally in the form of aqueous solution and drunk by the patient. The adjuvant can, however, also be administered parenterally, for instance by infusion. The preparation of infusion solutions is well known to the man skilled in the art and can be effected in a simple manner.

In the product or kit according to the invention the two components can be combined in each case in different manner. The adjuvant can be present in a form suitable for oral administration and/or for parenteral administration. For example, the agent may be present in the form of drink ampules or in the form of drink ampules which are diluted with water. The agent of the invention, for instance immune modulator liposomes, may be present in a form suitable for oral and/or parenteral administration. The combination is prepared in accordance with the purpose of the product. If the product is to be used for treatment, the product will contain the same number of dose units of adjuvant and agent, for instance liposomes. The number may, however, also vary. It is possible, for instance, for a product which is intended for diagnosis to contain several dose units of the adjuvant and only one or two dose units of the liposomes. The selection of the correct combination of the ratio of dose units of adjuvant and liposomes is well known to the man skilled in the art and depends on the intended use.

The adjuvant can be prepared in simple manner by simply mixing the components. The aldehyde selected is mixed with pharmacologically acceptable excipients and/or diluents, possibly together with the alcohol.

However it is preferred to prepare the adjuvant by irradiating an alcohol of formula II, $$RCH_2OH \qquad (II)$$

in which R is a hydrogen atom or a straight-chain or branched hydrocarbon group having 1 to 4 carbon atoms, with energy-rich radiation, with the admission of oxygen.

Gamma radiation, UV-radiation, x-radiation or electron radiation can be employed, for instance, as energy-rich radiation. In this connection the alcohols selected can be used as such or as alcohol/water mixtures, highly concentrated alcohol/water mixtures being particularly preferred as starting material. The irradiation is effected with admission of oxygen, and preferably admission of air.

An anti-tumor agent which is particularly important and effective in practice can be prepared, for instance, by exposing 96% ethanol in the presence of oxygen to energy-rich radiation of the type described until the desired amount of acetaldehyde has been formed. The solution then contains essentially, in addition to a large amount of ethanol, the acetaldehyde together with peroxides such as $H_2O_2$ or acetoperoxide or traces of peracetic acid as well as acetic acid. The last-mentioned substances substantially improve the action of the immune modulator charged liposomes. Surprisingly, that an increase typical for ethanol/acetaldehyde of the macrophages, T cells, T helper cells and killer cells was found and this effect deflects the direction of action of the immune modulators from a predominately B cell stimulation, such as is known, to an increase of the macrophages, T cells, T helper cells and natural killer cells, so that previously unknown large numbers of these cells are produced in humans. This is not described in the above-mentioned literature reference by U. Ehrenfeld, and was also not obvious.

For the immunological medicinal treatment, immune modulators lipidized, preferably in liposomes, suspended in sterile manner in physiological saline solution are administered by inhalation after prior oral administration of a cocktail consisting of preferably ethanol/acetaldehyde in water. This results in a clearly detectable reduction in the cancerous masses without adverse side effects.

If the immune modulator is tagged as mentioned above with a radioactive tracer, the visualizing of the Orphan distribution of 99 m technetium-tagged lipidized immune modulator molecules can preferably be recorded in the follow-up picture by the use of an external gamma camera.

If during the time of action of the tracer the oxygen given off into the tissue is increased by suitable agents, the action of earlier treatments can, in each case, be determined in advance by the external gamma camera.

In accordance with a particularly preferred embodiment of the invention, there is administered together with a cocktail and the tracer-tagged immune modulator liposomes "SmIL" an agent which increases the liberation of oxygen in the region of the malignant tumors. In this way the therapeutic radiation effect is at the same time increased. As such agents which increase the liberation of oxygen in the region of the malignant tumors there can be used all such agents with respect to which this effect is already known. Examples hereof are inositol hexaphosphate, glycerol diphosphate and other substances which, it is known, can be installed in the heme and have this effect there. The radiation treatment is limited to the intended place and the radiation can be individually dosed.

Intermediate phases or interruption, resp., in the radiation treatment are utilized for the treatment with lipidized immune modulators.

It was surprising and not obivous that the SmIL accumulates to such an extent on and in the malignant tumor. In this way a treatment of numerous different tumors is possible and it is also possible to detect and diagnose very small tumors in the body of mammals, particularly humans.

Accordance to the present invention it is thus possible for the first time to diagnose as well as cure malignant tumors in a simple manner without the patient being burdened in mammals, particularly humans. According to the invention, it is possible to irradiate the tumors in targeted fashion with practically no injury to neighboring tissue and, furthermore, one can, according to the invention, apply medication, for instance the cytostatics or immune modulators, at the place where they are actually to act.

For testing and treatment, a substantially glucose-free and starch-free diet is necessary. The effect of the active combination is eliminated locally by glucose, sugar, starch, vitamin C in high doses and vitamin $B_1$, and in general by cortisone and antihistamines.

On each day of treatment, one-half to a full dose of the aerosol is inhaled and one dose of the cocktail drunk. The data for the aerosol and cocktail refer to a daily dose.

The aerosol: The liposomes are single unilamellar vesicles which consist of phosphatidyl choline : phosphatidyl serine : cholesterol in a molar ratio of 8:2:10 and have radii of less than 300Å; 5 mg thereof are suspended in 5 ml of physiologicalsaline solution for inhalation. The liposomes bear an immune modulator, for instance 6 μg/ml from Nocardia opaca, which is present in an amount of 1% to 2% within and to an amount of 98% to 99% on the outside of the liposomes. For a scintigraphic diagnosis and for radiation therapy the immune modulator bears a tagging of 25 to 50 mCi of 99 m technetium-pertechnetate and for the color diagnosis of cancer, alone or together with the tracer, a suitable dyestuff. For the immune treatment of malignant tumor diseases and the therapy of conditions of cellular and humoral lowered immune defense, the immune modulator bears no tracer.

The cocktail: 25 to 50 ml of a combination of 96% ethanol and hyperpure acetaldehyde in a ratio of 1000 to 40 ml are diluted with 250 to 500 ml of tap water.

Very small amounts of tumor can be precisely displayed. The tumor size of a malignoma is unimportant for the success of the display. Phosphatidyl choline (lecithin) occurs in the lungs, physiologically saturated with fatty acids. It serves for the stabilizing of the alveola walls. As lipid on the immune modulator molecules it serves, in particular, for facilitating their passage; ethanol and acetaldehyde are known as pore expanders on membranes in living tissue and support this effect of the lecithin.

After the passage through the alveola wall of the lung the lipidized immune modulator is brought, via blood and lymph vessels, to the malignant tumors where it is bound in it primarily by an active process of the living cancer-cell wall. The immune modulator is detectable histologically there by ordinary methods of staining in the manner of granula; ordinary lipid stains show only minimum sporadic indications for lipid. The lipids are probably substantially lost upon passage through the cell walls.

Fluorescein isothiocyanate or 99 m Tc remain bound to the immune modulator up to the cancer cell wall and are detectable there by fluorescence microscope or autoradiographically,resp.

Various melanosarcomas, squamous cell carcinomas and adenocarcinomas of the female breast were displayed with the test by means of the external gamma camera. The tests were repeated with simple means in a hospital outside the university clinic and were easily reproducible with the same results for the immune modulators from BGC and Nocardia SmIl tested there.

Bone-enclosed metastases were not detectable by the test; in case of partial extension out of the bone, photographing was possible. Brain metastases can be displayed but in this case the administration of the cocktail must be dispensed with since it immediately induces extensive colliquation necroses on cerebral metastases. Tumors and metastases outside the basal membrane of the skin were not detectable by the test.

In the case of intratumoral administration of SmIL, only diffusion display occurred in the case of healthy tissue while in the case of malignant tissue there was the same long-term bonding and photographability for days as upon the inhalation of SmIL.

The local necrotizing process of tumor tissue after inhalation of SmIL with local inflammation and resorptive increase in temperature to 38.5° C. was always reproducible with Nocardia and BCG upon administration of the cocktail and insufflation of oxygen for several hours under fine-needle biopsy control.

In connection with SmIL administration for the tests with the gamma camera there were always obtained, as in the above -mentioned immune treatment, leukocytoses with increase in the number of macrophages, Rieder's, T, T helper and natural killer cells as well as the lymphatic plasma cells. In the case of one young woman, the inhalation of SmIL (after drinking the cocktail as in the above-mentioned cases) led to an increase in the leukocytes in the blood from 6000 to 25,000/$\mu$l without increase in temperature or other signs of illness.

In case of weaknesses of the cellular and humoral immune defense, the number and activity of the macrophages, T and T helper cells in particular increased to twice their initial values after administration of the cocktail and to 6 times more after additional inhalation of the lipidized immune modulator, with shift of the ratio of the T helper to T suppressor cells in the direction towards the T helper cells; B cells and immunoglobulin production also increased. These effects occur equally on healthy patients and on patients suffering from cancer. The number of Rieder's cells and monocytes, which in a normal person is 140/$\mu$l, increased to twice this number after administration of the cocktail consisting of ethanol/acetaldehyde and water; when MDP in liposomes was inhaled for the cocktail (30 $\mu$g in 5 mg), it increased to 900/$\mu$l and when immune modulator from Nocardia (ImmL) in liposomes (30 $\mu$g in 5 mg) was inhaled additionally to the cocktail, to values around and above 2000/$\mu$l; in the case of elderly patients and patients suffering from cirrhosis of the liver, the values were about half those of younger people.

The immune response in the cases treated in this manner is constant with respect to the cellularly and humorally increased reaction.

Exhaustion of the immune system was not observed, nor overreactions or indications of degeneration. The tolerance appears excellent.

The disferarance of liver metastases within days to weeks which takes place after the use of the agent claimed always led rapidly to a clear improvement in the general condition of the patient.

After the administration of acetaldehyde, there take place, as is known, at the cell surfaces interlinkings of $NH_2$ groups, and at times decreases in the blood sugar level; in all cases the $\beta$-oxidation of fatty acids took place. The metabolism products obtained upon the lipolysis act, in part, similar to acetaldehyde.

The phagocyte performance of the macrophages upon the destruction of cells of malignant tumors is significantly increased upon the use of acetaldehyde and ImmL in the manner indicated. The disappearance of skin metastases and liver metastases and the conversion of lung metastases into aerated structures was noted. A significant macrophage suppuration was found in the histology on the surfaces of malignant tumors. The effect of x-radiation on tumor tissue is improved by acetaldehyde/ethanol. The action of acetaldehyde and ImmL in the above-indicated manner of use is dependent on quantity; rapidly growing malignant tumors respond better than slowly growing ones. The action of the preferred combination in accordance with the invention of ethanol/acetaldehyde in aqueous solution together with liposomes which are tagged and/or charged with medication, preferably immune modulators, will be explained below by way of example in the description of the pathophysiological picture of cancer patients. The differences upon the use of the combination of the invention for recognition and treatment as compared with the untreated cancer patients can be summarized as follows:

Detection: The tagging concerns malignant tumor tissue.

Treatment:

a) Subjective (Evaluation by patient): Freedom from pain, feeling of well-being.

b) Clinical: At times a slight increase in size, but also a decrease in size of the tumor regions, sometimes within hours and sometimes within days, and in some cases also complete disappearance of tumors and their metastases within months: Restoration of gross strength, normalization of oxygen absorption and utilization, visibly healthy appearance, normalization of the liver function (laboratory values) in the region of the tumor hyperthermia with the body temperature otherwise being normal, typical sweating, return of nerve function in the case of nerves which had failed due to the tumor, reduction of the inflammatory reaction in the vicinity of the tumors; after involuntary placebo test (20 days), during which time there was an increased growth in the size of the metastasis in the lungs and severe dyspnea, after another larger dose of the agent, excretion in the urine of grams of triple phosphate, whereupon there was again a clear improvement in the respiration and in the general condition.

The individual phases of the diagnosis and treatment can be described as follows in one individual case:

1st Phase:

The patient, H.A., was a 67 year old male. In Jan. of 1981 "carcinoma of the retrolingual tonsillar region" was diagnosed. The histological findings were: squamous cell carcinoma, moderately strongly keratinizing and moderately differentiated. The clinical stage was $T_3N_2M_0$. A few days later, a typical operation was performed with tumor resection, partial removal of the lower jaw bone and radical "neck dissection" on the left side.

Resection did not reach sound tissue everywhere. Thereafter the patient received the typical radiation treatment with an average dose of a total of 60 Gy. One week after the end of the radiotherapy, there was bleeding from esophageal varices, grade IV, which was controlled conservatively. In Feb. of 1982, an en-bloc-reresection of a local tumor recidivism with submental lymph adenectomy was performed. The histological finding was the same. Thereupon, local x-radiation treatment was employed with a focal dose of 30 Gy.

In Mar. 1982, because of a pronounced swelling of the rest of the tongue 50 ml of an adjuvant cocktail of 96% ethanol and highly pure acetaldehyde in a ratio of 1000 ml to 40 ml, was administered daily in an amount of 50 ml in water. Accompanying this, a low-glucose diet was maintained. This resulted in the desired relief. The leukocyte count—which had previously been between 3000 to 4000/$\mu$l- increased as a result of this treatment to 4000 to 5000/$\mu$l. Lymphocyte irritation cells (Rieder), lymphatic plasma cells and young monocytes were found in an amount of up to 4% in the differential white blood count.

2nd Phase:

In July 1982, a tumor node the size of a cherry could be palpated in the left submental region. The patient inhaled a suspension of liposomes with MDP each day for three weeks for purposes of immune stimulation. The leukocyte count increased to values of about 5000 per $\mu$l.

In the differential white blood count, the Rieder cells and the young monocytes increased to 6%. After these three weeks, the tumor node was removed. The histological findings showed significant macrophage suppuration in addition to the known carcinoma.

3rd Phase:

After 14 days without treatment, tumor metastases the size of a quail's egg were found for the first time in the monthly control x-ray of the lung. Liver metastases and an enlargement of the spleen were found sonographically. Thereupon cytostatic chemotherapy was immediately introduced for 5 days.

A second series, two months later, had to be interrupted after the first day of treatment because of life-threatening complications. Between and after the chemotherapy series, the above-mentioned adjuvant cocktail and immune-stimulating inhalations were administered intermittently.

4th Phase:

Since Feb. 1983, the cocktail, the low-glucose diet and an inhalation of liposomes which contained a different derivative of MDP were used each day. The leukocyte count increased to an average of 6000/$\mu$l. The differential white blood count showed Rieder lymphocytes and young monocytes in an amount of 15%. These two types of cells decreased relatively in number when the leukocyte count increased to 9000/$\mu$l and increased when the leukocyte count was at 4000/$\mu$l.

A daily rate of Rieder lymphocytes and young monocytes of 900/$\mu$l blood was found. A plum-sized metastasis, which had developed in the horizontal scar on the left neck in Jan. of 1983 disappeared in April 1983 without the formation of additional scars. The pus contained macrophages. The same was noted in the case of another skin metastasis and a lymph node metastasis. The round shadows in the lung x-ray pictures became continuously larger from Feb. 1983 to the end of May 1983.

During the same period of time, the patient stated that he was free of pain and felt well. Because of the amount of macrophages continuously produced, the increase in size of the lung metastases without the formation of new metastases led to the idea that the growth could be due in part to the formation by macrophages of a capsule around the metastases.

On May 3, 1983, the patient was subjected to a scintigraphic test after inhalation of liposomes charged with immune modulators, tagged with 99 m Tc. The aerosol-contained 50 mCi. The patient was scanned with a nuclear Chicago gamma camera which was provided with a high resolution 140 KeV parallel collimator and a Simis 3-data system (Informatek, Birmingham, Ala., USA). Ten second dynamic scannings were carried out continuously for one hour.

From the resultant pictures, the localization of the radioactivity was determined for the region of interest. An hour after the application of the 99 m Tc liposomes by aerosol, 1.5% of the radioactivity was found in the lung. The balance was found in the upper respiratory tract and in the larynx. Computer subtraction of the background activity permits a clear visualization of the metastases. The liposome tracer is present predominantly in the pre-bronchial region. It shows an asymmetry of distribution which corresponds very precisely to the x-ray pictures.

At this time, about 5% of the lung radioactivity was found in the circulation, as shown by the gamma camera scanning of the legs of the patient. Four hours after the inhalation of the 99 m Tc liposome suspension, increased radioactivity was found in the circulation and in the digestive tract. This may be due to the dissociation of the 99 m Tc and the binding of this tracer to molecules which are able to pass through capillary walls. At no time was a concentration of radioactivity found in the liver. In June of 1983, liver metastases could not be found sonographically.

5th Phase:

In Sep. of 1983 there was a pronounced attack of cirrhosis of the liver which had already been known prior to the carcinosis. After a 14-day interruption of the treatment as a result thereof, a liver metastasis of somewhat less than 3 cm in diameter was found sonographically. In the x-ray control picture of the lung, a few new metastases of bean size were found alongside of air-filled structures in old lung metastases which were in the course of breakdown.

For an exclusive treatment with, for instance, ethanol/acetaldehyde in aqueous solution and immune modulator-loaded liposomes (for instance with muramylic-acid dipeptide derivatives MDP) a malignant tumor mass, for example melanosarcoma, of a total of 150 g,is curable in case of a good immune reaction of the patient and a period of treatment of half a year, provided that a tumor does not acquire a protective mechanism against the new situation.

By means of free 99 m Tc, there was a change in enrichment of radioactivity in a thyroid adenoma, which it was possible to eliminate. After the elimination of the free 99 m Tc, a metastasis of a melanosarcoma was found in this adenoma.

The diagnosis was effected with 40 mCi tagging in the first of the following cases and with 25 mCi tagging in the second.

In one case of a female patient with a melanosarcoma, the scintigraphic test showed a known been-sized melanoma node in the musculature of the left side of the neck, another known melanoma node in an adenoma of the right thyroid and one melano node of the size approximately of a barley corn in the prevertebral fatty tissue in the center of the thorax. By the treatment, local metastases of the melanoma on the left thigh, inguinal lymph node metastases on both sides and para-aortal lymph node metastases disappeared in this case.

In this patient, there was noted scintigraphically the inside of the uterus with existing menstruation and the nipple-close ends of the milk ducts; no pathological event is present there. In the case of another patient in whom, a few weeks before the test, a melanosarcoma of the right foot and a lymph-node package with metastases from the right thigh had been resected histologically in the sound tissue, the scintigraphical test showed in the right and left thighs throughout the entire lymph region very small accumulations of cells of the sarcoma and furthermore sarcoma cell spreadings in the arthrosis region of both knees; angiography did not show any blood-vessel relationship to the accumulation of tumor cells. The regions of resorption of the sarcoma resection places, despite the existence still of edema, did not show any radiation. Nor was there pictured a fresh inflammation from the vein puncture of the previous day, a resorptive inflammation around suture material in the depth of the left palm, or the two arthrotic hip joints. After administration of oxygen for two hours in the evening after the scintigraph an inflammatory reaction in the region of the tracer-marked places had developed by the morning of the following day in the sense of a radiation over-reaction.

In the case of the patient first described on the preceding page, a three-month treatment with cocktail and ImmL was carried out daily after the test, whereupon a new test was carried out with SmIL after administration of the cocktail, which test now showed—considerably smaller—only the melanoma node in the thyroid-gland adenoma. The thyroid-gland adenoma with the melanoma node and the lymph nodes in the musculature of the left cervical region were removed surgically after the test. Histology could still note only a few melanoma cells in the node in the thyroid gland and did not note any melanoma cells in the node in the cervical region. Autoradiography was clearly positive in the case of the node in the thyroid-gland adenoma and slightly positive in the node from the left cervical region. The tagged cells appear to be morphologically normal in part.

This same normalizing of the morphology of melanoma cells was (clinically and histologically) observed histologically at the edge of a melanoma after the administration of a cocktail before another operative removal. Here, prior to the giving of the cocktail the melanotically colored region had been tagged; 12 hours later the melanotically colored region was almost 1 cm within the tagging.

This patient has now been free of recurrence for five months without ImmL. The cocktail treatment and diet was started in her case in the final stage 9 years ago. The patient has been able to work again since 8 years.

In the case of the second patient described in the text of the last page, there was a recurrence of cherry size near the groin on the right thigh 5 months after the radiation over-reaction. Within a month, the node grew to 3 times its size. It was partially removed surgically. Within three weeks there was local recidivism of the same size as prior to the operation, and, at a distance of 5 to 10 cm away, two metastases of cherry size formed.

The computer tomogram showed, in addition, a densification in the pelvis minor on the right side. The patient showed clinical indications of an obstruction of bile ducts in the liver.

Upon the test with cocktail and SmIL there was found a clear accumulation scintigraphically in the right thigh and in the right pelvis minor.

By fine-needle bioptic and suction-bioptic histological and autoradiographic control it was possible, after oxygen insufflation for several hours, to discover already after a few days, as a result of the bonding of the tracer by the immune modulator at the cancer cell walls, a continuously increasing number of damaged and necrotic melanoma cells and an increase in the locally present lymphocytes, macrophages and granulocytes. The effect goes hand in hand with local hyperthermia, general increase in temperature to 38.5° C. for a period of two days and subjectively a "feeling of a slight cold." After effecting this treatment four times in 14 days the clinically visible metastases started fibrosing and the intrahepatic bile duct obstruction was eliminated.

EXAMPLE 1

Preparation of a tagged immune modulator

To 30 μg of a commercially obtainable immune modulator which is present together with tin chloride in slight excess to the number of amino groups of the immune modulator in lyophilized form under nitrogen, 100 mCi 99 m Tc in physiological saline solution are added at room temperature. The reaction mixture is set aside for 5 minutes.

Under nitrogen ($N_2$):

30 μg of the immune modulator are applied separately to 5 mg of liposomes suspended in 2.5 ml of physiological saline solution. The two mixtures are added to each other, mixed and set aside for 10 minutes. The product obtained can be used directly for diagnosis and therapy.

EXAMPLE 2

Preparation of immune modulator which is tagged with a dyestuff:

Preparation of 1000 doses for the color diagnosis of malignant tumor tissue.

1.947 mg of fluorescein isothiocyanate (molecular weight 389.4) are dissolved in 50 ml of pure ethanol and mixed with 30 mg immune modulator from Nocardia opaca (molecular weight 60000), dissolved in 5000 ml of water, mixed and set aside for one hour at 37° C. In order to separate the stained product from unreacted dyestuff it is introduced into a separating column having a cross section of 18 mm, which contains 50 g of Sephadex G-50. Buffered to a pH of 8 with physiological saline solution, it is eluted and the unreacted dyestuff is retained in the separation column. The eluate is then lyophilized, obtaining about 1000 doses.

For the preparation of the color diagnosis solution the contents of the puncture bottle containing 5 mg of a lipid mixture corresponding to about 1 mmole of a lipid mixture of phosphatidyl choline : phosphatidyl serine : cholesterol in a molar ratio of 8:2:10 in the form of liposomes with radii of less than 300Å, suspended in 5 ml of physiological saline solution, are removed with a syringe by the user and filled into the puncture bottle with 31.947 μg of the lyophilized fluorescein-isothiocyanate tagged immunomodulator from Nocardia opaca. Aside from the substances indicated, nitrogen is present in the puncture bottles (as also in the puncture bottles which, for diagnosis and therapy with 30 μg immune modulator to 5 mg liposomes of the above-indicated composition and size which are suspended in 5 ml of physiological saline solution, as well as in the puncture bottles which contain, in lyophilized form, tin chloride and the immune modulator). The resultant solution is set aside for 10 to 20 minutes whereupon it is ready for use. The mixing and setting aside take place in a black shipment carton—ultraviolet light prematurely reduces the efficiency of the fluorescein 1 mole of the immune modulator binds at least 10 moles of the FITC.

EXAMPLE 3

Different forms of administration:

(a) 30 μg of immune modulator from Nocardia opaca lyophilized, available on the market.

(b) 5 mg of lipid mixture, phosphatidyl choline: phosphatidyl serine : cholesterol in a molar ratio of 8:2:10 are prepared.

This lipid mixture is preferably in the form of liposomes with radii of less than 300Å, suspended in 2.5 to 5 ml of physiological saline solution.

(c) 31.947 μg of lyophilized fluorescein isothiocyanate-tagged immune modulator from Nocardia opaca.

(d) 1.128 μg tin chloride ($SnCl_2 \times 2H_2O$) together with 30 μg of immune modulator from Nocardia opaca, lyophilized.

Samples (a), (b), (c) and (d) may be present in puncture bottles which contain the substance in sterile form under nitrogen ($N_2$).

Substances (a) and (b) can be mixed with a double cannula for treatment. However, it is also possible to mix the substances previously and to store them in mixed condition and then use this for the treatment.

Samples (a), (b) and (d) are used for the nuclear-medical test in the manner that 100 mCi 99 m Tc in 1 ml of physiological saline solution is added to sample (d), whereupon samples (a) and (b) are either mixed with a double cannula or are taken already as mixture and the mixture is then added to the solution (d) in the double cannula.

Local radiation treatment is also carried out with such a combination.

Samples (b) and (c) can furthermore be mixed with the double cannula for the color test.

I claim:

1. An agent for the diagnosis and treatment of malignant tumors and for the treatment of reduced cellular and humoral immune defense, comprising a pharmaceutical carrier and an a immune modulator which is an extract from bacteria or a mixture of bacteria extracts, wherein the bacteria are selected from the group consisting of Norcardia rubra, Nocardia opaca, Calmette-Guerin bacillus and salmonella, and which immune modulator is (1) tagged with a radioactive tracer, dyestuff or cytostatic or a mixture of such tagged immune modulators, or (2) tagged with a radioactive tracer, dyestuff or cytostatic or a mixture of such tagged immune modulators or tagged with tin-II-chloride (a) in and on liposomes or (b) in or on liposomes or (c) lipidized.

2. An agent according to claim 1 in a form suitable for oral or parenteral administration.

3. An agent according to claim 2, in a form suitable for inhalation.

4. An agent according to claim 1., containing a reagent which increases the liberation of oxygen in the region of the malignant tumors.

5. A agent according to claim 4, wherein the reagent is a member selected from the group consisting inositol hexaphosphate, pentaphosphate, tetraphosphate, triphosphate and glycerol diphosphate.

6. An agent according to claim 1 containing an adjuvant which is an alkehyde of the formula RCHO in which R is a hydrogen atom or a straight-chain or branched hydrocarbon group having 1 or 4 carbon atoms or a metabolically releasable precursor thereof in a pharmaceutically acceptable solvent.

7. An agent according to claim 6 wherein the adjuvant is in a form suitable for oral administration.

8. An agent according to claim 6 containing an alcohol of the formula $R^1CH_2OH$ in which $R^1$ is a hydrogen atom or a straight-chain or branched chain hydrocarbon group having 1 to 4 carbon atoms.

9. An agent according to claim 8, wherein the alcohol and the alkehyde are in a ratio of 1000 grams of alcohol to 15 to 40 grams alkehyde.

10. An agent according to claim 1, wherein the immune modulator is a synmethetic or semi synthetic modulator.

11. An agent according to claim 10 in the form of a solution containing an alkehyde of formula I

RCHO  (I)

in which R is a hydrogen atom or a straight-chain or branched hydrocarbon group having 1 to 4 carbon atoms, or a metabolically releasable precursor thereof, in a pharmaceutically acceptable solvent.

12. An agent according to claim 11, containing an alcohol of formula II

$R^1CH_2OH$  (II)

in which $R^1$ is a hydrogen atom or a straight-chain or branched hydrocarbon group having 1 to 4 carbon atoms.

13. An agent according to claim 12, wherein the alcohol and the alkehyde are in a ratio of 1000 g of alcohol to 15 to 40 g of alkehyde.

14. An agent according to claim 13 in a form suitable for oral or parenteral administration.

* * * * *